United States Patent [19]
Gohbayashi et al.

[11] Patent Number: 4,883,902
[45] Date of Patent: Nov. 28, 1989

[54] METHOD OF PRODUCING TETRAKIS[3-(3,5-DI-TERT-BUTYL-4-HYDROXYPHENYL)PROPIONYLOXYMETHYL]METHANE

[75] Inventors: Masayoshi Gohbayashi, Nakatsu; Noritsugu Narita, Suzuka; Makoto Maruno, Mie, all of Japan

[73] Assignee: Yoshitomi Pharmaceutical Industries, Ltd., Osaka, Japan

[21] Appl. No.: 275,175

[22] PCT Filed: Feb. 1, 1988

[86] PCT No.: PCT/JP88/00088
 § 371 Date: Sep. 28, 1988
 § 102(e) Date: Sep. 28, 1988

[87] PCT Pub. No.: WO88/05773
 PCT Pub. Date: Aug. 11, 1988

[30] Foreign Application Priority Data
 Feb. 3, 1987 [JP] Japan ................................ 62-24163

[51] Int. Cl.$^4$ ............................................. C07C 69/76
[52] U.S. Cl. ..................................................... 560/75
[58] Field of Search ........................................ 560/75

[56] References Cited
U.S. PATENT DOCUMENTS

| 3,779,945 | 12/1973 | Dexter | 560/75 |
| 4,396,552 | 8/1983 | Kinobloch et al. | 560/75 |
| 4,511,491 | 4/1985 | Ishii et al. | 560/75 |
| 4,547,585 | 10/1985 | Yamanaka et al. | 560/75 |
| 4,594,444 | 6/1986 | Orban | 560/75 |
| 4,683,326 | 7/1987 | Orban et al. | 560/75 |
| 4,716,244 | 12/1987 | Orban | 560/75 |

FOREIGN PATENT DOCUMENTS

| 9025349 | 9/1984 | Japan | 560/75 |
| 2201846 | 5/1987 | Japan | 560/75 |

Primary Examiner—Paul J. Killos
Attorney, Agent, or Firm—Wenderoth, Lind & Ponack

[57] ABSTRACT

A method of producing tetrakis[3-(3,5-di-tert-butyl-4-hydroxyphenyl)propionyloxymethyl]methane by ester exchange between a 3-(3,5-di-tert-butyl-4-hydroxyphenyl)propionic acid alkyl ester and pentaerythritol in the presence of a basic catalyst, which comprises carrying out the reaction in the presence of bis[2,2,2-tris(hydroxymethyl)ethoxylmethane.

According to the method of the invention, tetrakis[3-(3,5-di-tert-butyl-4-hydroxyphenyl)propionyloxymethyl]methane can be obtained in high yields and in high purity without using an excessively large amount of a 3-(3,5-di-tert-butyl-4-hydroxyphenyl)propionic acid alkyl ester which is an expensive compound, while controlling the formation of the byproduct to a minimum level.

1 Claim, No Drawings

METHOD OF PRODUCING TETRAKIS[3-(3,5-DI-TERT-BUTYL-4-HYDROXY-PHENYL)PROPIONYLOXYMETHYL]METHANE

FIELD OF THE INVENTION

This invention relates to a method of producing tetrakis[3-(3,5-di-tert-butyl-4-hydroxyphenyl)propionyloxymethyl]-methane [hereinafter sometimes referred to as "compound (I)"], which is in wide use as an antioxidant for polyolefins, among others.

DESCRIPTION OF THE PRIOR ART

It is known that the compound (I) can be produced by subjecting pentaerythritol and a 3-(3,5-di-tert-butyl-4-hydroxyphenyl)propionic acid alkyl ester [hereinafter sometimes referred to as "compound (II)"] to ester exchange in the presence of a catalyst such as an alkali metal lower alkoxide, wherein the compound (II) is used in an at least stoichiometric amount relative to pentaerythritol, namely in an amount of at least 4 moles per mole of pentaerythritol (Japanese Patent Publication No. 19083/1967).

As described in the above-cited patent specification, a product in which the hydroxyl groups of pentaerythritol have not been fully substituted, namely a tri-substituted pentaerythritol derivative of the formula

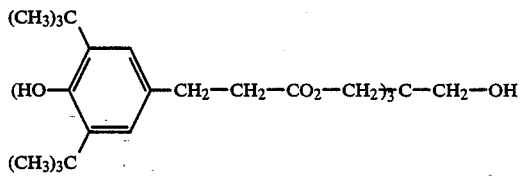

(III)

[hereinafter sometimes referred to as "byproduct"] is formed as a byproduct and contaminates the product compound (I) when this is produced by the above-mentioned method.

Formation of the impurity (III) as a byproduct naturally leads to decreased yields of the desired compound (I). Furthermore, the present inventors found that the byproduct (III) is difficult to separate from the compound (I) by ordinary recrystallization procedures, hence the purity of the product cannot be improved by conventional methods. Accordingly, it is very desirable from the industrial viewpoint if the formation of the byproduct (III) could be inhibited.

In the above-cited patent specification, it is suggested that the formation of the byproduct (III) might be controlled when the compound (II) is used in an at most 15% excess relative to the stoichiometrically required amount, namely in an amount of at most 4.6 moles per mole of pentaerythritol. Based on this suggestion, the present inventors detailedly investigated the relation possibly existing between the mole ratio of the compound (II) to pentaerythritol and the formation of the byproduct (III) and found that the yield of the byproduct (III) can be suppressed to about 10%, preferably 5% or less on the pentaerythritol basis when the compound (II) is used in an amount of 4.6 moles per mole of pentaerythritol. In that case, the subsequent purification step can give the desired product (I) in a form substantially free from the byproduct (III), but that portion of the relatively expensive compound (II) which remains unreacted necessarily means a loss, which leads to an increase in the cost of manufacturing the desired product.

DISCLOSURE OF THE INVENTION

The present inventors made intensive investigations in an attempt to solve the above problems and provide a method of producing the desired product (I) in a highly pure form and in good yields using the compound (II) and pentaerythritol as the starting materials by without using a excessively large amount of the compound (II), which is expensive, while controling the formation of the byproduct (III) to a minimum level. As a result, they have now completed the present invention.

The present inventors surprisingly found that when the ester exchange reaction between the compound (II) and pentaerythritol is carried out in the presence, in the reaction system, of 0.05–1.5% by weight of bis[2,2,2-tris(hydroxymethyl)ethoxy]methane (hereinafter sometimes referred to as "methylenebispentaerythritol") which is represented by the formula

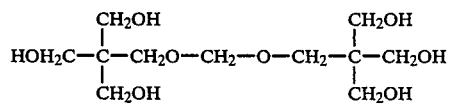

the formation of the byproduct (III) can be made minimal and the desired product (I) can be obtained in good yields.

Thus the invention provides a method of producing tetrakis[3-(3,5-di-tert-butyl-4-hydroxyphenyl)propionyloxymethyl]methane which comprises carrying out the ester exchange reaction between the propionic acid alkyl ester (II) and pentaerythritol in the presence of a basic catalyst and in the presence of bis[2,2,2-tris(hydroxymethyl)ethoxy]methane.

In accordance with the invention, the desired product (I) can be obtained in good yields by using the expensive compound (II) only in a slight excess, namely in an amount of 4.2–4.4 moles per mole of pentaerythritol, with the yield of the byproduct (III) being controlled to about 10% or less, preferably about 5% or less on the pentaerythritol basis. The subsequent purification by simple recrystallization can give the desired product (I) in a highly purified form. The methylenebispentaerythritol reacts in part with the propionic acid ester (II) to give a di- or tri- substituted derivative of the methylenebispentaerythritol. However, the yield of such product is very small and such product can be removed readily by recrystallization, hence the loss of the propionic acid ester (II) is minimal and the purity of the desired product is not lowered.

The constitution and advantages of the present invention will become more apparent from the detailed description which follows.

As the starting compound alkyl ester (II) having 1–4 carbon atoms to be used in practicing the invention, the methyl or ethyl ester is particularly preferred.

The compound (II) is preferably used in a stoichiometrically slight excess relative to pentaerythritol, namely in an amount of about 4.2–4.4 moles per mole of pentaerythritol. While the conventional methods allow the formation of the above-mentioned byproduct (III) in considerable amounts, which can hardly be removed by recrystallization and reduces the purity of the desired product (I), when the compound (II) is used in such extent of excess, the method of the invention makes it possible to obtain the desired product (I) in a highly pure form since the formation of the byproduct (III) is small in amount and this byproduct can be easily removed by simple recrystallization, as mentioned later herein.

In practicing the invention, an ester exchange catalyst is used. As said catalyst, there may be mentioned alkali or alkaline earth metal hydrides, such as sodium hydride, potassium hydride and lithium hydride; alkali metal lower alkoxides, such as lithium methoxide, sodium methoxide, potassium methoxide, lithium ethoxide, sodium tert-butoxide and potassium tert-butoxide; and organotin oxides such as dibutyltin oxide, monobutyltin oxide and tributyltin oxide. When used in amounts known to be sufficient in the art, such catalysts can give satisfactory results. Thus they are used generally in an amount of 0.1-10 parts by weight, preferably in an amount of 0.3-3 parts by weight, per 100 parts by weight of the compound (II). In conducting the ester exchange reaction in accordance with the invention, a solvent is preferably used. Usable solvents are, for example, dimethyl sulfoxide, dimethylformamide, tetrahydrofuran, dioxane, diglyme (2-methoxyethyl ether), dimethylacetamide, hexamethylphosphoramide, 1,2-dimethoxyethane, acetonitrile, tert-butanol, toluene, xylene, hexane and heptane. Among them, toluene and xylene are preferred The solvent is used in an amount of at most 5 parts by weight, preferably 0.1-10 parts by weight, per part by weight of the compound.

The most important element of the invention is that the methylenebispentaerythritol should be present, in an amount of 0.05-1.5% by weight on the pentaerythritol basis, in the reaction system in which the ester exchange reaction is to proceed. By employing such means, it becomes possible to control the yield of the above-mentioned byproduct (III) to about 10% or less, preferably a level below 5% on the pentaerythritol basis. When the methylenebispentaerythritol is used in an amount less than 0.05% by weight, the formation of the byproduct (III) is significant. When it is used in an amount exceeding 1.5% by weight, the reaction of the methylenebispentaerythritol with the compound (II) progresses to an extent which is no more negligible, whereby the expensive compound (II) is lost in vain and the yield of the desired product (I) upon recrystallization in the purification step to be mentioned later herein is significantly lowered.

In working the present invention, the ester exchange reaction is carried out until substantial cessation of the formation of the corresponding alcohol such as methanol or ethanol, generally at a temperature of 80°-200° C. for 5-20 hours. Said byproduct alcohol is removed, preferably instantaneously, from the reaction system by a conventional method generally employed in carrying out various ester exchange reactions, for example by distilling off under reduced pressure (e.g. 5-50 mmHg).

No particular apparatus is required. Any conventional reaction vessel equipped with a stirrer, a heating device and a device for distilling off the above-mentioned alcohol may be used.

The desired product (I) is then isolated and purified from the reaction mixture after completion of the ester exchange reaction. Preferred as the means of isolation and purification is recrystallization. As the solvent to be used in the recrystallization, there may be mentioned hexane, cyclohexane, heptane, methanol, ethanol, propanol, isopropanol, butanol and isobutanol. Among them, preferred is methanol or ethanol. The recrystallization solvent need not be pure. Thus, for instance, commercially available ethanol, which contains about 5% of water, can be used successfully.

Since the desired product (I) is present in the above-mentioned reaction product in high yields and the byproduct quantity is small, the above-mentioned isolation/purification procedure comprising recrystallization results only in a minimal loss.

The product (I) produced by the method of the invention as detailedly described hereinabove contains a minimal amount of the above-mentioned byproduct (III), hence is highly pure, and is best suited for use as an antioxidant, among others.

EXAMPLES

The following examples are further illustrative of the present invention but are by no means limitative thereof.

EXAMPLE 1

A one-liter four-necked flask equipped with a stirrer, a reflux condenser, a thermometer and a nitrogen gas inlet tube was charged with 300 g of toluene, 20 g of dibutyltin oxide, 44.2 g of pentaerythritol, 420 g of methyl 3-(3,5-di-tert-butyl-4-hydroxyphenyl)propionate (at least 99% pure) and 0.11 g of bis[2,2,2-tris(hydroxymethyl)ethoxy]methane, and the contents were heated with stirring at 170°-175° C. for 12 hours, while the byproduct methanol was distilled off with toluene. Thereafter, 300 g of toluene, 2.0 g of oxalic acid and 12 g of powdered cellulose (Solka Floc) were added and the mixture was heated under reflux for dehydration. The oxalate salt of dibutyltin oxide, insoluble in toluene, and the Solka floc were filtered off, and the toluene was distilled off under reduced pressure to give 420 g of a light-yellow syrupy substance. Analysis of this syrupy substance revealed that the yield of tetrakis[3-(3,5-di-tert-butyl-4-hydroxyphenyl)propionyloxymethyl]methane was 97.0% of the theoretical on the pentaerythritol basis and that of the byproduct 2.8% of the theoretical on the pentaerythritol basis.

The syrupy substance was then recrystallized from 95% methanol-water to give white crystals in 97% yield. They had a purity of not lower than 99%, and the content of the above-mentioned byproduct was below 1% by weight.

EXAMPLE 2 and EXAMPLES 3 and 4

The procedure of Example 1 was followed in the same manner except that bis[2,2,2-tris(hydroxymethyl)ethoxy]methane was used in an amount of 0.5% by weight (Example 2), 0.05% by weight (Example 3) or 1.5% by weight (Example 4).

The results thus obtained are shown in Table 1 in terms of the production yield and recovery yield of the desired product, the yield of the byproduct and the purity of the desired product, together with the results obtained in Example 1.

The crystals obtained in Examples 3 and 4 were again recrystallized from isopropanol. The purities of the thus obtained crystals were respectively the same as those shown in Table 1.

TABLE 1

|  | Yield of compound (I) (% of theoretical) | Yield of byproduct (III) (%) | Recovery in recrystallization (%) | Purity of crystals (I) (%) | Purity of crystals (III) (%) |
|---|---|---|---|---|---|
| Example 1 | 97.0 | 2.8 | 97 | 99 | 1 |
| Example 2 | 97.3 | 2.0 | 97 | 99 | 1 |
| Example 3 | 90.1 | 8.0 | 95 | 97 | 3 |
| Example 4 | 95.0 | 1.8 | 90 | 96 | 1 |

According to the method of the invention, the desired tetrakis[3-(3,5-di-tert-butyl-4-hydroxyphenyl)propionyloxymethyl]methane can be obtained in high yields and in high purity.

The present invention has been described in detail in the foregoing specification including Examples, which can be modified and varied to such an extent as not to conflict with the concept and the scope of the present invention.

What is claimed is:

1. A method of producing tetrakis[3-(3,5-di-tert-butyl-4-hydroxyphenyl)propionyloxymethyl]methane by ester exchange between a 3-(3,5-di-tert-butyl-4-hydroxyphenyl)propionic acid alkyl ester and pentaerythritol in the presence of a basic catalyst, which comprises carrying out the reaction in the presence of bis[2,2,2-tris(hydroxymethyl)ethoxy]methane.

* * * * *